United States Patent [19]

Keim et al.

[11] 4,400,551
[45] Aug. 23, 1983

[54] PROCESS FOR THE PRODUCTION OF ACETALDEHYDE AND ETHANOL

[75] Inventors: Karl-Heinz Keim, Heimerzheim; Joachim Korff, Bernheim-Sechtem, both of Fed. Rep. of Germany

[73] Assignee: Union Rheinische Braunkohlen Kraftstoff Aktiengesellschaft, Wesseling, Fed. Rep. of Germany

[21] Appl. No.: 294,293

[22] Filed: Aug. 19, 1981

[30] Foreign Application Priority Data

Aug. 21, 1980 [DE] Fed. Rep. of Germany ....... 3031558

[51] Int. Cl.$^3$ ............................................. C07C 45/49
[52] U.S. Cl. .................................................. 568/487
[58] Field of Search ............... 568/487, 484, 485, 489

[56] References Cited

U.S. PATENT DOCUMENTS

| | | | |
|---|---|---|---|
| 3,387,043 | 6/1968 | Kuraishi et al. | 568/487 |
| 4,190,729 | 2/1980 | Forster | 568/487 |
| 4,293,718 | 10/1981 | Gauthier-Lafaye et al. | 568/485 |
| 4,302,611 | 11/1981 | Porcelli | 568/484 |
| 4,306,091 | 12/1981 | Gauthier-Lafaye et al. | 568/487 |

FOREIGN PATENT DOCUMENTS

| | | | |
|---|---|---|---|
| 10373 | 4/1980 | European Pat. Off. | 568/487 |
| 22735 | 1/1981 | European Pat. Off. | 568/487 |

*Primary Examiner*—Werren B. Lone
*Attorney, Agent, or Firm*—Connolly and Hutz

[57] ABSTRACT

This invention relates to a process for the production of acetaldehyde and ethanol by reacting methanol with carbon monoxide and hydrogen at elevated temperature and pressure in the presence of a catalyst containing cobalt, biphosphine, biarsine or bistibine and hydrogen iodide and/or hydrogen bromide.

9 Claims, No Drawings

PROCESS FOR THE PRODUCTION OF ACETALDEHYDE AND ETHANOL

BACKGROUND OF THE INVENTION

Description of the Prior Art

It is known that the formation of homologs of methanol by reacting methanol with carbon monoxide and hydrogen under elevated temperature and pressure is promoted by catalysts containing cobalt and halogen compounds, particularly iodine compounds.

The additional use of ligands containing phosphorus, arsenic or antimony in the catalyst is also known. Thus, according to German Offenlegungsschrift No. 26 25 627 for example, cobalt iodide or acetate is used with tributyl phosphine and other phosphines.

Finally, homolog-forming reactions are also known in which biphosphines, biarsines and bistibines are used as catalyst ligands in the presence of cobalt and suitable halogen compounds. These are elemental iodine or bromine, covalent compounds such as, for example, methyl iodide or bromide, and also ionic compounds, such as cobalt iodide or cobalt bromide, or those of the type which are required to contain cations that are inert with respect to the hydrocarbonylation reaction, such as sodium, potassium, lithium iodides or bromides (EPA o olo 373).

The yields of the particularly valuable products, acetaldehyde and ethanol, obtained by the known processes are unsatisfactory. Accordingly, the object of the present invention is to improve the product yields hitherto achieved.

SUMMARY OF THE INVENTION

According to the present invention, this object is achieved by a process in which methanol is reacted with carbon monoxide and hydrogen at elevated temperature and under a pressure in the range from 200 to 450 bar in the presence of a catalyst containing cobalt, as ligands, a biphosphine, biarsine or bistibine and hydrogen iodide and/or hydrogen bromide and 0.009 to 0.0005 mole of hydrogen iodide and/or hydrogen bromide being used per mole of methanol used.

DESCRIPTION OF SPECIFIC EMBODIMENTS

The reaction pressure is in the range from 200 to 450 bar, advantageously in the range from 230 to 400 bar and, more particularly in the range from 280 bar to about 350 bar.

The synthesis gas is generally used in a ratio of carbon monoxide to hydrogen of 1:1, although this ratio may also be varied within wide limits from 4:1 to 1:4.

The reaction temperature is in the range from about 100° to 250° C. and, with particular advantage, in the range from 190° to 210° C.

The residence time may be between 10 and 200 minutes and is advantageously between 30 and 90 minutes.

The cobalt component of the catalyst may be formed by finely divided elemental cobalt, $Co_2(CO)_8$, and also by cobalt salts, such as for example cobalt acetate, cobalt propionate, cobalt bromide, cobalt iodide, cobalt formate etc., which form cobalt carbonyl complexes or hydrocobalt carbonyl complexes with carbon monoxide or with carbon monoxide and hydrogen. The molar ratio of cobalt to methanol used is from 0.005 to 0.0001 and, with particular advantage, from 0.003 to 0.0005.

Suitable ligands are the biphosphines normally used in the prior art, for example those corresponding to the following general formula $$\begin{array}{c} R_1 \\ \diagdown \\ R_2 \end{array} P{+}(CH_2)_n{-}P \begin{array}{c} R_3 \\ \diagup \\ \diagdown \\ R_4 \end{array}$$

in which $R_1$ to $R_4$ may be alkyl, aryl, aroxyl, alkoxyl, alkylamine, arylamine or cyclic compounds. The number n of carbon atoms between the phosphorus atoms may amount to between 1 and 6. However, the carbon bridge between the phosphorus atoms may also be cyclic for example and may contain heteroatoms like N, P, O and S or even unsaturated groups. $R_1$-$R_4$ in the cases of alkyl, alkoxyl and alkylamine may have 1-12 C-atoms; in the cases of aryl, aroxyl and arylamine the aromatic ring is a phenyl-ring which can be substituted by alkyl-groups with 1-6 C-atoms; monocyclic rings as substituents may have 5-12 C-atoms and bicyclic rings as substituents may have 10-20 C-atoms.

The molar ratio of phosphorus to methanol used is from 0.006 to 0.0001 and advantageously from 0.003 to 0.0005. The same applies to biarsines, bistibines and compounds in which the donor atoms are nitrogen.

The halogen component is added in the form of hydrogen iodide and/or hydrogen bromide to the catalyst containing cobalt or cobalt compounds and biphosphine, biarsine or bistibine. Hydrogen iodide and/or hydrogen bromide may of course also be added in solution, for example in the form of a 50 to 60% aqueous solution. Hydrogen iodide and/or hydrogen bromide may also be used for example in the form of phosphonium or ammonium salts.

Hydrogen iodide and/or hydrogen bromide (instead of halogen compounds used in the prior art in the presence of biphosphines, biarsines or bistibines as ligands) in the system lead not only to surprisingly high yields of acetaldehyde and ethanol, but—unlike other halogen additives, such as iodine or bromine for example—afford the technically important advantage that the system is considerably less corrosive.

Solvents, such as for example hydrocarbons or even oxygen-containing solvents, are not necessary for the reaction according to the invention, although they may be used.

EXAMPLE 1

50 ml (1.24 moles) of methanol, 480 mg of Co (acetate)$_2$. 4 H$_2$O, 510 mg of the biphosphine, bis-diphenyl phosphinoethane, and 250 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 200° C., the pressure amounted to 285 bar.

After cooling and working up, including hydrolysis of the acetals and esters, it was found that 73 mole percent of the methanol used had reacted. After hydrolysis of the acetals and esters formed, the reaction mixture contained—based on the methanol reacted—46 mole percent of acetaldehyde, 34 mole percent of ethanol, 2 mole percent of dimethyl ether, 7.5 mole percent of acetic acid and 11.5 mole percent of residues with C>2.

By repeating this example but with the addition of methyl iodide instead of hydrogen iodide, the reaction mixture obtained, consisted of only 42 mole percent of acetaldehyd and 29.5 mole percent of ethanol.

EXAMPLE 2

50 ml (1.24 moles) of methanol, 480 mg of Co (acetate)$_2$. 4 H$_2$O, 510 mg of the biphosphine, bis-diphenyl phosphinoethane, and 429 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 200° C., the pressure amounted to 245 bar. The gas mixture continued to be introduced over a reaction time of 1 hour so that the pressure was kept at 245 bar. After cooling and working up, it was found that 76 mole percent of the methanol used had reacted. After hydrolysis of the acetals and esters formed, the reaction mixture contained—based on the methanol reacted—42 mole percent of acetaldehyde 32 mole percent of ethanol, 3.5 mole percent of dimethyl ether, 12.0 mole percent of acetic acid and 11.5 mole percent of compounds with C>2.

EXAMPLE 3

50 ml (1.24 moles) of methanol, 320 mg of Co (acetate)$_2$. 4 H$_2$O, 255 mg of bis-diphenyl phosphino-ethane and 429 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 200° C., the pressure amounted to 220 bar. The gas mixture continued to be introduced over a reaction time of 1 hour to keep the pressure at 220 bar.

After cooling and working up, it was found that 65 mole percent of the methanol had reacted. The product contained 43 mole percent of acetaldehyde, 30 mole percent of ethanol, 3 mole percent of dimethyl ether, 9 mole percent of acetic acid and 15 mole percent of products with C>2.

EXAMPLE 4

50 ml (1.24 moles) of methanol, 480 mg of Co (acetate)$_2$. 4 H$_2$O, 510 mg of bis-diphenyl phosphino-ethane and 250 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 180° C., the pressure amounted to 255 bar. The gas mixture continued to be introduced over a reaction time of 80 minutes so that the pressure was kept at 255 bar.

After cooling and working up, it was found that 71 mole percent of the methanol used had reacted. The product contained 42 mole percent of acetaldehyde, 28 mole percent of ethanol, 3 mole percent of dimethyl ether, 10 mole percent of acetic acid and 17 mole percent of products with C>2.

EXAMPLES 5

50 ml (1.24 moles) of methanol, 480 mg of Co (acetate)$_2$. 4 H$_2$O, 546 mg of bis-dipenyl phosphino-butane and 250 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 200° C., the pressure amounted to 260 bar. The gas mixture continued to be introduced over a reaction time of 60 minutes so that the pressure was kept at 260 bar. After cooling and working up, it was found that 81 mole percent of the methanol used had reacted. The product contained 46 mole percent of acetaldehyde, 33 mole percent of ethanol, 2 mole percent of dimethyl ether, 11 mole percent of acetic acid and 8 mole percent of products with C>2.

EXAMPLE 6

50 ml (1.24 moles) of methanol, 480 mg of Co (acetate)$_2$. 4 H$_2$O, 510 mg of bis-diphenyl phosphino-ethane and 250 mg of a 57% hydrogen iodide solution were introduced into a stirrer-equipped autoclave. A 1:1-mixture (parts by volume) of carbon monoxide and hydrogen was introduced under pressure in such a way that, after heating to 180° C., the pressure amounted to 305 bar. The gas mixture continued to be introduced over a reaction time of 80 minutes so that the pressure was kept at 305 bar. After cooling and working up, it was found that 76 mole percent of the methanol used had reacted. The product contained 43 mole percent of acetaldehyde, 28 mole percent of ethanol, 3 mole percent of dimethyl ether, 11 mole percent of acetic acid and 15 mole percent of products with C>2.

EXAMPLE 7

50 ml (1.24 moles) of methanol, 230 mg of Co (acetate)$_2$. 4 H$_2$O, 200 mg of bis-diphenyl phosphino-ethane and 250 mg of a 57% aqueous hydrogen iodide solution were introduced into a stirrer-equipped autoclave. A 1:1-mixture (parts by volume) of carbon monoxide and hydrogen was introduced under pressure in such a way that, after heating to 200° C., the pressure amounted to 255 bar. The gas mixture continued to be introduced over a reaction time of 1 hour so that the pressure was kept at 255 bar. After cooling and working up, including hydrolysis of the acetals and esters, it was found that 63 mole percent of the methanol used had reacted. After hydrolysis of the acetals and esters formed, the product contained—based on the methanol reacted—49 mole percent of acetaldehyde, 36 mole percent of ethanol, 2 mole percent of dimethyl ether, 5 mole percent of acetic acid and 8 mole percent of residues with C>2.

We claim:

1. In a process for the production of acetaldehyde and ethanol by reacting methanol with carbon monoxide and hydrogen at a temperature of between 100°-250° C. and under elevated pressure in the presence of a catalyst containing cobalt, an iodine and/or bromine compound and a phosphorus-containing ligand, the improvement which comprises reacting methanol with carbon monoxide and hydrogen under a pressure of from 200 to 450 bar in the presence of a catalyst containing cobalt, a halogen compound selected from the group consisting of hydrogen iodide and hydrogen bromide, using 0.009 to 0.0005 mole of hydrogen iodide and/or hydrogen bromide per mole of methanol used, and a biphosphine of the formula

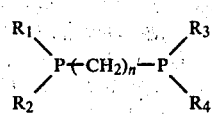

wherein R$_1$ to R$_4$ are each alkyl of 1–12 carbon atoms, alkoxy of 1–12 carbon atoms, alkylamine of 1–12 carbon atoms, aryl, aroxyl or arylamine each of 6 carbon atoms unsubstituted or substituted by alkyl of 1 to 6 carbon atoms, monocyclic rings of 5 to 12 carbon atoms or bicyclic rings of 10 to 20 carbon atoms, and n is the integer from 1 to 6.

2. The improvement in accordance with claim 1, wherein from 0.005 to 0.0008 of hydrogen iodide and/or hydrogen bromide is used per mole of methanol.

3. The improvement in accordance with claim 1, wherein the pressure is in the range from 230 to 400 bar.

4. The improvement in accordance with claim 1, wherein the pressure is in the range from 280 to 350 bar.

5. The improvement in accordance with claim 1, wherein the molar ratio of cobalt to methanol is from 0.005 to 0.0001.

6. The improvement in accordance with claim 1, wherein the molar ratio of cobalt to methanol is from 0.003 to 0.0005.

7. The improvement according to claim 1, wherein the molar ratio of phosphorus to methanol is from 0.006 to 0.0001.

8. The improvement according to claim 1, wherein the molar ratio of phosphorus to methanol is from 0.003 to 0.0005.

9. The improvement according to claim 1, wherein the reaction time is from 30 to 90 minutes.

* * * * *